United States Patent
Addington et al.

(10) Patent No.: US 6,561,195 B2
(45) Date of Patent: *May 13, 2003

(54) LARYNGOSCOPE NEBULIZER FOR APPLICATION OF CHEMOSTIMULANT TO PATIENT'S LARYNX TO STIMULATE INVOLUNTARY COUGH REFLEX

(75) Inventors: W. Robert Addington, Melbourne Beach, FL (US); Robert E. Stephens, Kansas City, MO (US); Stuart P. Miller, Melbourne Beach, FL (US)

(73) Assignee: Pneumoflex Systems L.L.C., Melbourne, FL (US)

( * ) Notice: Subject to any disclaimer, the term of this patent is extended or adjusted under 35 U.S.C. 154(b) by 75 days.

This patent is subject to a terminal disclaimer.

(21) Appl. No.: 09/817,806

(22) Filed: Mar. 26, 2001

(65) Prior Publication Data

US 2001/0050086 A1 Dec. 13, 2001

Related U.S. Application Data

(63) Continuation-in-part of application No. 09/734,404, filed on Dec. 11, 2000, which is a continuation of application No. 09/224,431, filed on Dec. 31, 1998, now Pat. No. 6,267,729, which is a continuation of application No. 08/885,360, filed on Jun. 30, 1997, now Pat. No. 5,904,656, which is a continuation of application No. 08/559,562, filed on Nov. 16, 1995, now Pat. No. 5,678,563.

(60) Provisional application No. 60/192,175, filed on Mar. 27, 2000.

(51) Int. Cl.$^7$ ................................................. A61B 5/08
(52) U.S. Cl. ..................................... 128/898; 600/529
(58) Field of Search ................................. 600/187, 188, 600/199, 529; 128/897, 898

(56) References Cited

U.S. PATENT DOCUMENTS 4,273,112 A * 6/1981 Heine et al. ................ 600/199
4,432,350 A * 2/1984 Breslau et al. .............. 600/187
6,267,729 B1 * 7/2001 Addington et al. ......... 128/898

* cited by examiner

Primary Examiner—Eric F. Winakur
Assistant Examiner—David J. McCrosky
(74) Attorney, Agent, or Firm—Allen, Dyer, Doppelt, Milbrath & Gilchrist, P.A.

(57) ABSTRACT

A laryngoscope-associated arrangement provides for focused delivery of a chemostimulant from a nebulizer through a delivery conduit to a patient's larynx to allow a practitioner to directly observe the function of the patient's larynx during the course of delivery of the chemostimulant. This not only provides the practitioner with a visualization of whether the patient's laryngeal vestibule is functioning properly, but allows the practitioner to be satisfied that the chemostimulant is accurately delivered to the intended region of interest.

16 Claims, 1 Drawing Sheet

Figure 1:
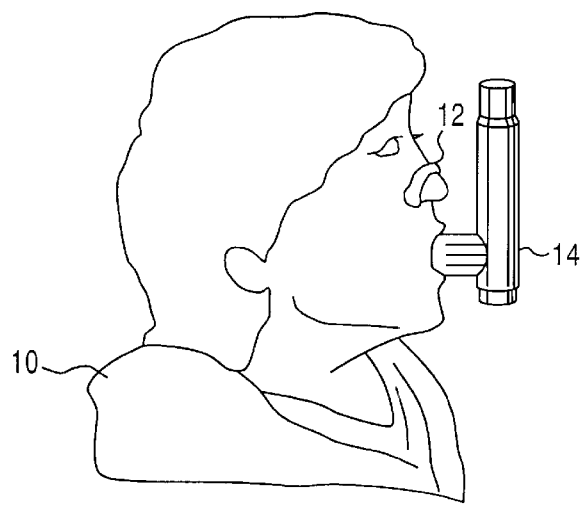

LARYNGOSCOPE NEBULIZER FOR APPLICATION OF CHEMOSTIMULANT TO PATIENT'S LARYNX TO STIMULATE INVOLUNTARY COUGH REFLEX

CROSS-REFERENCE TO RELATED APPLICATION

The present application is a continuation-in-part of co-pending U.S. patent application, Ser. No. 09/734,404 (hereinafter referred to as the '404 application), filed Dec. 11, 2000, entitled: "Aspiration Screening Process for Assessing Need for Modified Barium Swallow Study," by W. Robert Addington et al, which is a continuation of U.S. patent application, Ser. No. 09/224,431, filed Dec. 31, 1998 now U.S. Pat. No. 6,267,729, which is a continuation of U.S. patent application, Ser. No. 08/885,360, filed Jun. 30, 1997, now U.S. Pat. No. 5,904,656, which is a continuation of U.S. patent application, Ser. No. 08/559,562, filed Nov. 16, 1995, now U.S. Pat. No. 5,678,563, the disclosures of which are incorporated herein.

In addition, the present application claims the benefit of U.S. Provisional Patent Application, Ser. No. 60/192,175, filed Mar. 27, 2000, by W. Robert Addington et al, entitled: "Laryngoscope Nebulizer for Application of Chemostimulant to Patient's Larynx to Stimulate Involuntary Cough Reflex," and the disclosure of which is incorporated herein.

FIELD OF THE INVENTION

The present invention relates in general to the field of speech pathology, and is directed to determining whether a patient is at risk for one or more abnormal physiological conditions, including but not limited to oral or pharyngeal dysphagia, and pneumonia. In particular, the present invention is directed to an enhancement to the invention disclosed in the above-referenced '404 application, that provides focusing or 'targeting' delivery of the chemostimulant to stimulate nociceptor (irritant) and c-fibre receptors in the patient's throat, through a relatively narrow diameter tube that may be coupled with the observation tube of a laryngoscope. Coupling this nebulizer tube with that of the observation tube of a laryngoscope facilitates direct visualization of the mucosa of the laryngeal vestibule through a laryngoscope during inhalation and/or the laryngeal cough reflex, to determine whether the patient's larynx is functioning normally or abnormally.

BACKGROUND OF THE INVENTION

As described in the above-referenced '404 application, the conventional technique employed by speech pathologists for clinically identifying patients at risk for aspiration has involved the evaluation of a patient's swallow. A normal human swallow can be separated into four phases: 1)—oral preparation, 2)—the oral phase, 3)—the pharyngeal phase, and 4)—the esophageal phase. Patients who have suffered a stroke, traumatic brain injury or neuromuscular disorder (such as MS or ALS) have an increased risk of aspiration, and may have difficulty with either the oral phase, the pharyngeal phase or both, secondary to neurologic deficits.

Poor tongue movement in chewing or in the swallow can cause food to fall into the pharynx and into the open airway before the completion of the oral phase. A delay in triggering the pharyngeal swallowing reflex can result in food falling into the airway during the delay when the airway is open. Reduced peristalsis in the pharynx, whether unilateral or bilateral, will cause residue in the pharynx after the swallow that can fall or be inhaled into the airway. Laryngeal or cricopharyngeal dysfunction can lead to aspiration because of decreased airway protection during the swallow.

An abnormal human swallow is termed dysphagia. The oropharyngeal physiology involved in a normal swallow is very complicated, and many different neurological disturbances can disrupt normal swallowing and can cause aspiration of food material, liquid or solid, into the lungs, leading to increased morbidity in hospitalized patients and possible pneumonia. See, for example, the article by Jeri Logemann, entitled: "Swallowing Physiology and Pathophysiology," Otolaryngologic Clinics of North America, Vol. 21, No. 4, November 1988, and the article by L. Kaha et. al., entitled: "Medical Complications During Stroke Rehabilitation, Stroke Vol. 26, No. 6, June 1995.

Speech pathologists have tried many procedures to detect or predict aspiration in patients with neurological deficits. Although the standard bedside swallow exam to screen patients is beneficial for evaluating patients at risk for oral or pharyngeal dysphagia, studies have shown that, when compared to a modified barium swallow (MBS) videofluoroscopic examination, it is neither very specific nor sensitive in detecting aspiration. (The MBS test customarily involves having the patient ingest a volume of barium in a semi-solid or liquid form. Through fluoroscopy, the travel path of the swallowed barium may be observed by a medical practitioner to determine whether any quantity has been aspirated— which could lead to acute respiratory syndrome or pneumonia.) See, for example, the article by Mark Splaingard et. al. entitled: "Aspiration in Rehabilitation Patients: ideofluoroscopy vs. Bedside Clinical Assessment; Archives of Physical Medicine and Rehabilitation, Vol. 69, August, 1988, and the article by P. Linden, et. al., entitled" "The Probability of Correctly Predicting Subglottic Penetration from Clinical Observations", Dysphagia, 8: pp 170–179, 1993.

As discussed in the above-referenced Logemann article, and also in an article entitled: "Aspiration of High-Density Barium Contrast Medium Causing Acute Pulmonary Inflammation—Report of Two Fatal Cases in Elderly Women with Disordered Swallowing," by C, Gray et al, Clinical Radiology, Vol. 40, 397–400, 1989, videofluoroscopic evaluations are more costly than bedside evaluations and videofluoroscopy is not entirely without risk. Because of the poor predictability of bedside exams, the MBS is being used more and more with its increased reliability for diagnosing aspiration. Many studies using videofluoroscopy have tried to pinpoint the exact anatomical or neurological deficit causing the dysphagia, as well as what stage of the swallow is primarily affected in different disorders.

Patients with a head injury, stroke or other neuromuscular disorder can aspirate before, during, or after the swallow, and a high percentage can be silent aspirators. Unfortunately, these patients might not display any indication of aspiration during a clinical exam, but can be detected by the MBS, as discussed in the Logemann article and in an article by C. Lazurus et al, entitled: "Swallowing Disorder in Closed Head Trauma Patients," Archives of Physical Medicine and Rehabilitation, Vol. 68, February, 1987, an article by J. Logemann, entitled: "Effects of Aging on the Swallowing Mechanism," Otolaryngologic Clinics of North America, Vol. 23, No. 6, December 1990, and an article by M. DeVito et. al., entitled: "Swallowing Disorders in Patients with Prolonged Orotracheal Intubation or Tracheostomy Tubes," Critical Care Medicine, Vol. 18, No. 12, 1990.

The bedside swallow exam that has been customarily performed by most speech pathologists evaluates history, respiratory status, level of responsiveness and an oral exam. The oral examination includes a detailed evaluation of the muscles of mastication, lips, tongue, palate, position in which the patient is tested, as well as swallowing evaluation. Sensation, various movements and strength are carefully evaluated. In the pharyngeal stage, the patient is tested for a dry swallow, thin liquid, thick liquid, pureed textures and solid textures.

A typical bedside exam looks for nasal regurgitation, discomfort or obstruction in the throat or multiple swallows, as well as any visible signs that may indicate risk for aspiration, gurgling, impaired vocal quality, and coughing. The bedside exam results are then analyzed to determine whether the patient should have an MBS study to evaluate swallowing physiology and to rule out aspiration. Although the bedside exam is very thorough, and can identify patients who are at risk for or have dysphagia, it is not effective in determining which patients will aspirate.

In addition to the foregoing, speech pathologists have historically had difficulty studying the sensory afferents of the larynx involved in airway protection. As described in an article by J. Widdicombe et al, entitled: "Upper Airway Reflex Control," Annual New York Academy of Science, Vol. 533, 252–261, 1988, the sensory afferents for general coughing travel the internal branch of the superior laryngeal nerve. A patient may have a voluntary cough present with the efferent motor system intact, but not have any sensation on the larynx secondary to the afferents becoming completely or partially affected, which would be indicative of risk for silent aspiration.

Although an MBS test is of value to patients that silently aspirate, it is difficult to decide which patients should have an MBS test. Not all patients with a closed head injury or a stroke will aspirate. Moreover, it is not economically realistic to employ an MBS test to evaluate all patients with neurologic deficits for aspiration. Advantageously, the chemostimulant-based, cough-invoking screening process described in the '404 application and its parent predecessors, referenced above, successfully overcomes shortcomings of such conventional processes that have attempted to detect aspiration in patients with neurological deficits.

Referring to FIG. 1, pursuant to the invention disclosed in these applications, a patient 10 (wearing a nose clip 12) is subjected to an chemostimulant-based, inhalation cough test. In this test, a prescribed quantity of a chemostimulant that stimulates nociceptor (irritant) and C-fibre receptors of the patient's larynx is injected into the patient's mouth. Inhalation of the chemostimulant may be readily accomplished by using a standard nebulizer 14, that has been loaded with an aerosol chemostimulant, such as an atomized solution of tartrate mixed with saline. Not only has this solution has been demonstrated to stimulate a cough 100% of the time in normal individuals, but tartrate is considered safe, does not cause pain or discomfort, and has not been shown to cause bronchoconstriction or complications in asthmatics when inhaled in an aerosol form.

The quantity of chemostimulant is injected into the patient's mouth for a prescribed period of time (e.g., on the order of 15 seconds). The nebulizer output spray rate may be on the order of 0.2 ml/min. as a non-limiting example. The patient may be tested a prescribed number of times (e.g., up to three times) at different stimulant strengths until a cough is elicited. During each successive chemostimulant application, the patient receives progressively increasing concentrations of the aerosol for the prescribed period of time by tidal breathing at one minute intervals using successively increasing percentage concentrations (e.g. 20, 50 and 80 percent).

Once a cough is elicited from the patient as a result of the inhaled aerosol stimulant, the patient's response to the inhalation test is graded. The patient may be graded as being at low risk for pneumonia (where the patient coughs immediately in response to the initial aerosol spray) or at a high risk for pneumonia (where a cough is present but decreased, or the patient does not readily cough in response to the initial concentration spray, but requires a more concentrated aerosol application).

SUMMARY OF THE INVENTION

Now although the chemostimulant-based, cough-invoking screening process described in the '404 application is effective to determine whether a patient is at risk for one or more abnormal physiological conditions, including but not limited to oral or pharyngeal dysphagia, and pneumonia, it may be desirable to provide the practitioner with the ability to focus delivery of the chemostimulant to a particular region of the throat and directly observe that region of the patient's airway during the course of delivery of the chemostimulant. This would not only provide the practitioner with a visualization of whether a particular region of the patient's throat (in particular, the laryngeal vestibule) is functioning properly, but it would allow the practitioner to be satisfied that the chemostimulant is accurately delivered to the intended region of interest.

In accordance with the present invention, this objective is successfully accomplished by coupling the delivery port of the chemostimulant nebulizer with a throat insertable conduit. This conduit provides for focused delivery of the chemostimulant to that region of the patient's throat (the mucosa of the laryngeal vestibule) to be visualized by a monitoring device such as a laryngoscope. The chemostimulant conduit may comprise a relatively narrow flexible tube of the type used for airway-invasive procedures, so that the delivery port of the chemostimulant delivery tube may be inserted adjacent to the targeted and observed region of the throat.

To this end, the chemostimulant-delivery tube may be physically coupled with the laryngoscope observation tube, so that both tubes may be simultaneously inserted into the patient's airway; alternatively, it may be fed separately of the laryngoscope tubing to the observation region. In either case, the invention provides for focused delivery of chemostimulant and direct visualization of the laryngeal vestibule through the laryngoscope during inhalation and/or the laryngeal cough reflex, to enable the practitioner to determine whether the patient's larynx is functioning normally or abnormally.

BRIEF DESCRIPTION OF THE DRAWINGS

FIG. 1 diagrammatically illustrates the use of an aerosol inhaler in the chemostimulant-based, inhalation cough test disclosed in the '404 application; and FIG. 2 diagrammatically illustrates the coupling of a throat insertable conduit at the output port of a chemostimulant nebulizer with the observation tubing of a laryngoscope to provide focused delivery of chemostimulant to a visualized region of patient's throat.

DETAILED DESCRIPTION

As pointed out above, the present invention provides an enhancement to use of a chemostimulant to stimulate nociceptor (irritant) and c-fibre receptors in the patient's throat as described in the above-referenced '404 application, by coupling the delivery port of the chemostimulant nebulizer with a throat insertable conduit. This serves to achieve focused delivery of the chemostimulant to that region of the patient's throat (the mucosa of the laryngeal vestibule) being visualized by a device such as a laryngoscope, and allows a medical practitioner to visually monitor the functioning of the patient's airway in the course of determining whether the patient is at risk to one or more abnormal physiological conditions, such as oral or pharyngeal dysphagia, and pneumonia.

Figure 2:
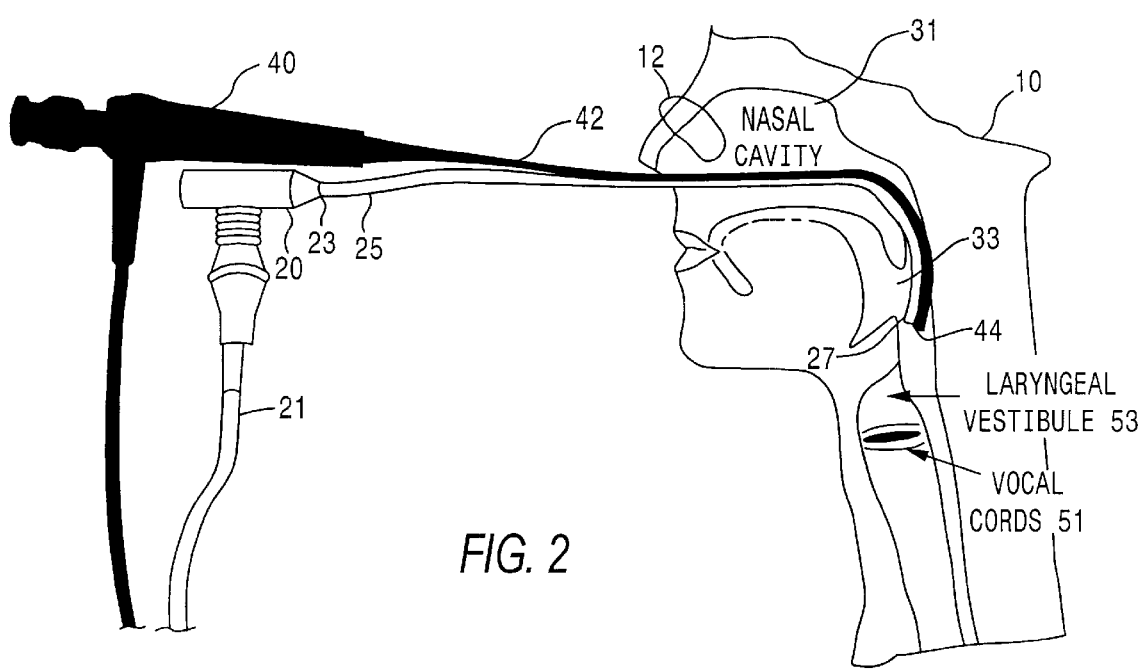

In accordance with a non-limiting embodiment the laryngoscope-associated, focused chemostimulant delivery process of the invention, diagrammatically illustrated in FIG. 2, the patient 10 may wear a nose clip 12, as in the inhalation cough test of FIG. 1, described above. The nebulizer, shown at 20, may comprise a standard pneumatically controlled atomizer device, that is supplied with an aerosol chemostimulant, such as a solution of twenty percent concentration by volume of tartrate mixed with saline, described in the '563 patent. As pointed out above, this solution has been demonstrated to stimulate a cough one-hundred percent of the time in normal individuals; also tartrate is considered safe, does not cause pain or discomfort, and has not been shown to cause bronchoconstriction or complications in asthmatics when inhaled in an aerosol form.

To control its operation, the nebulizer 20 is coupled via a pneumatic control input line 22 to a pulse atomizing pneumatic source (not shown). In accordance with the invention, nebulizer 20 has its output port 23 fitted with a length of relatively narrow chemostimulant delivery conduit 25. The conduit 25 may comprise a section of flexible tubing of the type used for airway-invasive procedures, so that it may be readily fed through the patient's airway, such as the patient's nasal cavity 31, with a distal end 27 of the conduit 25 placed adjacent to a targeted and visually observable region of the patient's throat 33.

To facilitate its use with a laryngoscope, shown at 40, the chemostimulant-delivery tube 25 may be physically coupled with an associated length of the laryngoscope's observation tube 42, as by means of a flexible adhesive or other attachment medium, so that both tubes may be simultaneously inserted into the patient's airway and fed to a desired observation, chemostimulation region (shown as being in proximity of the patient's vocal cords 51 and laryngeal vestibule 53). Alternatively, the chemostimulant-delivery tube 25 may be fed separately of the laryngoscope tubing 42 to the region of interest.

In either case, the chemostimulant delivery tube 25 is fed into the patient's airway such that the distal end 27 of the tube is positioned adjacent to the distal end 44 of the laryngoscope's tube 42. This ensures that delivery of the chemostimulant to the target region of the patient's throat, such the laryngeal vestibule 53, may be directly observed through the laryngoscope 40 during inhalation and/or the laryngeal cough reflex, and enable the practitioner to determine whether the patient's larynx is functioning normally or abnormally.

Similar to the inhalation test performed in accordance with the methodology described in the '563 patent, controlled pulsing of the nebulizer 20 causes a prescribed quantity of atomized chemostimulant to be injected (through the delivery conduit 25) into the patient's airway. However, unlike the mouth-based injection scheme of the '563 patent, the use of the conduit 25 at the output of the nebulizer 20 provides for 'focused' delivery of the chemostimulant directly to the region of the patient's throat to be stimulated. Being coupled with and terminated at the distal end 44 of the laryngoscope observation tubing 42 enables the chemostimulant delivery conduit 25 to target the atomized spray within a confirmed region being visualized through the laryngoscope 40, and thereby allows the medical practitioner to visually monitor the functioning of the patient's airway (e.g., laryngeal vestibule).

Again, the patient may be tested a prescribed number of times at different stimulant strengths until a cough is elicited. During successive chemostimulant injections, the patient may receive progressively increasing concentrations of the chemostimulant within the aerosol mixture, using successively increasing percentage concentrations (e.g. 20, 50 and 80 percent) of chemostimulant. Once a cough is elicited from the patient as a result of the inhaled aerosol mixture, the patient's response to the inhalation test may be graded, as in the patient evaluation process detailed in the '583 patent.

Again, the patient may be tested a prescribed number of times at different stimulant strengths until a cough is elicited. During successive chemostimulant injections, the patient may receive progressively increasing concentrations of the chemostimulant within the aerosol mixture, using successively increasing percentage concentrations (e.g. 20, 50 and 80 percent) of chemostimulant. Once a cough is elicited from the patient as a result of the inhaled aerosol mixture, the patient's response to the inhalation test may be graded, as in the patient evaluation process detailed in the '533 patent.

As will be appreciated from the foregoing description, coupling the delivery port to a chemostimulant nebulizer with a throat insertable conduit not only enables focused delivery of the chemostimulant to a targeted region of the patient's throat (e.g., the mucosa of the laryngeal vestibule) but, when coupled with the observation tubing of a monitoring device such as a laryngoscope, allows a medical practitioner to visually monitor the functioning of the patient's airway during chemostimulant injection.

While we have shown and described an embodiment in accordance with the present invention, it is to be understood that the same is not limited thereto but is susceptible to numerous changes and modifications as known to a person skilled in the art. We therefore do not wish to be limited to the details shown and described herein, but intend to cover all such changes and modifications as are obvious to one of ordinary skill in the art.

What is claimed is:

1. A method of evaluating a patient, the method comprising:

providing a substance which when delivered adjacent the larynx of the patient is effective to stimulate a sensory innervation associated with the patient's larynx and thereby elicit an involuntary cough in a patient who does not suffer from a prescribed abnormal physiological condition;

providing a monitoring instrument through which the patients larynx may be monitored;

inserting a delivery conduit from a substance delivery device into the patient to a location adjacent the larynx;

delivering said substance through said delivery conduit; and externally monitoring the patient's larynx using said monitoring instrument, to observe a response thereof to the delivery of said substance.

2. The method according to claim 1, further including evaluating the response of the patient to the delivered substance and determining presence of the prescribed physiological condition of the patient other than the patients ability to cough.

3. The method according to claim 1, further comprising inserting into the patient a monitoring conduit from said monitoring instrument to thereby monitor the patient's larynx.

4. The method according to claim 3, wherein said monitoring instrument comprises a laryngoscope.

5. The method according to claim 1, wherein said substance delivery device comprises a nebulizer adapted to deliver a predetermined amount of an aerosol of said substance containing a chemostimulant effective to stimulate a sensory innervation associated with the patient's larynx and elicit an involuntary cough in a patient who does not suffer from said prescribed abnormal physiological condition.

6. The method according to claim 1, wherein said substance comprises a composition effective to stimulate an irritant receptor selected from the grouping consisting of a nociceptor, a C-fibre receptor, and combinations thereof.

7. The method according to claim 1, wherein said substance contains tartrate.

8. The method according to claim 1, wherein said prescribed abnormal physiological condition comprises at least one of dysphagia, aspiration, or aspiration pneumonia.

9. A test arrangement for identifying a risk of a patient to a prescribed abnormal physiological condition comprising:
   a predetermined quantity of a substance which, upon being delivered to the patient's throat adjacent the patient's larynx in an individual who does not suffer from said prescribed abnormal physiological condition, is effective to stimulate a sensory innervation and elicit an involuntary cough from said patient;
   a monitoring instrument through which the patient's larynx may be monitored; and
   a device that is adapted to deliver said substance through a delivery conduit insertable into the patients throat to a location adjacent the patient's larynx, a response of which to delivery is externally monitored by way of said monitoring instrument.

10. The test arrangement according to claim 9, wherein said monitoring instrument is coupled with a monitoring conduit that is insertable into the patient to a location through which said larynx may be monitored by way of said instrument.

11. The test arrangement according to claim 10, wherein said delivery conduit and said monitoring conduit are arranged to be insertable together to said location.

12. The test arrangement according to claim 9, wherein said monitoring instrument comprises a laryngoscope.

13. The test arrangement according to claim 9, wherein said substance delivery device comprises a nebulizer adapted to deliver a predetermined amount of an aerosol of said substance containing a chemostimulant effective to stimulate a sensory innervation associated with the patient's larynx and elicit an involuntary cough in a patient who does not suffer from said prescribed abnormal physiological condition.

14. The test arrangement according to claim 9, wherein said substance comprises a composition effective to stimulate an irritant receptor selected from the group consisting of a nociceptor, a C-fibre receptor, and combinations thereof.

15. The test arrangement according to claim 9, wherein said substance contains tartrate.

16. The test arrangement according to claim 9, wherein said prescribed abnormal physiological condition comprises at least one of dysphagia, aspiration, or aspiration pneumonia.

* * * * *

UNITED STATES PATENT AND TRADEMARK OFFICE
CERTIFICATE OF CORRECTION

PATENT NO.    : 6,561,195 B2
DATED         : May 13, 2003
INVENTOR(S)   : W. Robert Addington, Robert E. Stephens and Stuart P. Miller It is certified that error appears in the above-identified patent and that said Letters Patent is hereby corrected as shown below:

<u>Title page,</u>
Item [56], References Cited, U.S. PATENT DOCUMENTS,
Insert:

| | | | |
|---|---|---|---|
| -- 4,558,710 A | 12/1985 | Eichler | 600/553 |
| 5,024,087 A | 6/1991 | McConnel | 600/593 |
| 5,143,087 A | 9/1992 | Yarkony | 600/593 |
| 5,678,563 A | 10/1997 | Addington et al | 600/529 |
| 5,904,656 A | 5/1999 | Addington et al | 600/529 |

OTHER PUBLICATIONS,

Fujimura et al., "Sex Differences in the Inhales Tartaric Acid Cough Threshold in Non-atopic Healthy Subjects" 1990, Thorax, 45:633-634.

Horner et al., "Silent Aspiration Following Stroke," Neurology, vol. 38, pp. 317-319.

DePippo et al., "Validation of the 3-oz Water Swallow Test for Aspiration Following Stroke," Archives of Neurology, vol. 49, pp. 1259-1261.

Florida Hospital Association 1996--"Cost of Dysphagia Testing and treatment of Aspirating Pneumonia" (single sheet) dated Sep. 24, 1997.

Merck Index. 12th ed. 1996 "Tartaric Acid", p. 1552. United States Department of Labor, Occupational Safety and Health Administration. Material Safety Data Sheet on Tartaric Acid (2 sheets).

Addendum to MSDS on Tartaric Acid. "Regulatory Status"(6 sheets).

Partial Listing of OTC Inhalers with Bitartrate. (Single Sheet).

Patty's Industrial Hygiene and Toxicology vol. 2C 1982 "Tartaric Acid" pp 4937,4743-5, 4981-2.

Chasseaud LF. Down WH, Kirkpatrick D. 1977 Absorption and Biotransformation of L(+)-Tartaric Acid in Rats. Experientia 33:998-1003.

Fassett DW. Organic Acids. Anhydrides, Lactones, Acid Halides and Amides, Thioacids in Industrial Hygiene and Toxicology 2nd ed. vol. II. DW Fassett and DD Irish, eds., Wiley-Interscience, New York 1963. pp. 1771-7, 1811, 1814.

Fithugh OG, Nelson AA. 1947 The Comparative Chronic Toxicities of Fumaric, Tartaric, Oxalic and Maleic Acids. J AM Pharm Assocs 36:217-9.

Horn HJ, Holland EG, Hazleton LW. 1957 Safety of Adipic Acid as Compared with Citric and Tartaric Acid. J Agric Food Chem 5:759-61.

Lewis JD. 1977 Comparison of the Distribution of L(30 ) and DL-Forms of Tartatic Acid in the Rat. Acta Pharmacol Toxicol 41: 144-5.

Locke A, Locke RB, Schlesinger H, Carr H. 1942 The Comparative Toxicity and Cathartic Efficiency of Disodium Tartrate and Fumarate, and Magnesium for the Mouse and Rabitt, J AM Pharm Assoc 31;12-14.

Smyth Jr. HF, Carpenter CO, Weill CS, Pozzani UC, Striegel JA. 1962 Range-Finding Toxicity Data: List VL Am Ind. Hyg. Assoc J23:95-107.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Sourkes TL. Koppanvi T. Correlation Between the Acute Toxicity and the Rate of Elimination of Tartaric Acid and Certain of its Esters 1950. J AM Pharm Assoc. 39;275-6.

Underhill FP, Leonard CS Gross EG, Jaleski. TC. 1931. Studies on the Metabolism of Tartrates: II The Behavior of Tartrate in the Organism of the Rabbit, Dog, Rat and Guinea Pig. J. Pharmacol 43:359-80.

Weiss JM. Downs CR, Corson HP. 1923 Inactive Malic Acid as a Food Acidulent. Ind Eng Chem 15:629-30. Also cited by Registry of Toxic Effects of Chemical Substances, NIOSH ed., 1978.

WHO Food Additives Series, No. 5, "Toxicological Evaluation of Some Food Additives Including Anticaking Agents, Antimicrobials, Antioxidants, Emusifiers and Thickening Agents" [17th Report of the Joint FAO/WHO Expert Committee on Food Additives, SHO Technical Report Series, 1974, No. 539; FAO Nutrition Meetings Report Series, 1974, No. 53] Geneva. pp. 14, 222-4, 236-7, 512-4.

Addington WR, Stephens RE, Ockey RR, Kann D, Rodriguez M. A New Aspiration Screening Test to Assess the Need for Modified Barium Swallow Study. Archives of Physical Medicine and Rehabilitation Nov. 1995;76(11):1040.

Addington WR, Stephens RE, Gilliland K. Miller SP. The Laryngeal Evoked Potential (LEP) and Laryngeal Cough Reflex, Muscle and Nerve, Aug. 1997; 20(3); 1071-1072.447.

Alberts MJ, Horner J, Gray L. Brazer SR. Aspiration After Stroke: Lesion analysis by Brain MRI Dysphagia. 7(3):170-3, 1992.

Alessi DM, Berci G. Aspiration and Nasogastric Intubation. Otolaryngology--Head and Neck Surgery. 94(4):486-9, Apr. 1986.

Aubert M. Guilhen C. Topographie des Projections de la Senibilite Viscerale Sur L' ecorce Cerebrale du Chat.3. Etude des Projections Corticales du Nerf Larynge Superieur Archives Italiennes de Biolgie Nov. 1971:109(3):236-52.

Bandler R. Tork I. Midbrain Periaqueductal Grey Region in the Cat has Afferent Connections with Solitary Tract Nuclei. Neuroscience Letters Feb 10, 1987; 74(1):106.

Barillot JC, Mei N. Modification, Au Niveau du Noyau du Faisceau Solitaire, de l'Excitabilite des Terminaisons de Fibres Vagales ou Laryngees d'origine connue. 1964 Etude Unitaire, pp. 395-396.

Berger AJ. Dorsal Respiratory Group Neurons in the Medulla of Cat: Spinal Projections, Responses to Lung Inflation and Superior Laryngeal Nerve Stimulation. Brain Research Oct. 28, 1977; 35(2):231-54.

Berkley KJ, Schofield SL. Relays from the Spinal Cord and Solitary Nucleus Through the Parabrachial Nucleus to the Forebrain in the Cat. Brain Research Oct. 8, 1990; 529 (1-2): 333-8.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Boushey HA, Richardson PS, Widdicombe JG. Reflex Effects of Laryngeal Irritation on the Pattern of Breathing and Total Lung Resistance. Journal of Physiology Jul. 1972;224(2);501-13.

Boushey HA, Richardson PS. Widdicombe JF, Wise JC. The Response of Laryngeal Afferent Fibers to Mechanical and Chemical Stiimuli. Journal of Physiology Jul. 1974;240(1):153-75.

Callanan D, Dixon M, Widdicombe JG, Wise JC. Responses of Geese to Inhalation of Irritant Gases and Injections of Phenyl Diguanide, Respiration Physiology (1974) pp. 157-166.

Car A. Jean A. Roman C A. Pontine Primary Relay for Ascending Projections of the Superior Laryngeal Nerve. Exp. Brain Res. 1975; 22:197-210.

Choudry NB, Fuller RW. Sensitivity of the Cough Reflex in Patients with Chronic Cough. European Respiratory Journal 5(3)296-300, Mar. 1992.

Chung, K. Ambrogio F. Sant Ambrogio G. The Fiber composition of the Superior Laryngeal Nerve. FASEB Journal 1993;7:A402.

Daniels SK. Brailey K, Priestley DH, Herrington LR, Weisberg LA. Foundas AL. Aspiration in Patients with Acute Stroke. Arch Phys Med Rehabil vol. 79, Jan 1998, pp. 14-19.

Das RM, Jeffery PK. Widdicombe JG. The Structure and Function of Intra-Epithelial Nerve Fibers of the Respiratory Tract in the Cat [proceedings]. Journal of Physiology Aug. 1977;270(1):39P-40P.

Buchholz DW. Dysphagia Associated with Neurological Disorders [Review] Acta Oto-Rhino-Laryngologica Belgica. 48(2):143-55, 1994.

DePippo KL, Holas MA. Reding MJ. Validation of the 3-oz. Water Swallow Test for Aspiration Following Stroke. Arch. Neurol. Feb. 1994, vol. 5, pp. 119-120.

Dvachenko YE, Preobrazhensky NN. Funktsional'naia Differentsiatsiia Afferentov Verkhnegortannogo Nerve Koshki. [Russian: Functional Differentiation of Afferents of Superior Laryngeal Nerve in the Cat]. Neirofiziologiia 1984;16(6):777-83.

Droulias C, Tzinas S. Harlaftis N, Akin JT Jr. Gray, SW, Skandalakis, JE. The Superior Laryngeal Nerve. American Surgeon Sep. 1976:42(0:635-8.

Fujmura M, Sakamoto S, Kamio Y, Matsuda T. Cough Receptor Sensitivity and Bronchial Responsiveness in Normal and Asthmatic Subjects. European Respiratory Journal Mar. 1992;5(3);291-5.

Fujimura M, Sakamoto S, Kamio Y, Effects of Methacholine Induced Bronchoconstriction and Procateral Induced Bronchodilation of Cough Receptor Sensitivity to Inhaled Capsaicin and Tartaric Acid. Thorax Jun. 1992;47(6);441-5.

Fujimura M. Sakamoto S. Kamio Y, Matsuda T. Sex Difference in the Inhaled Tartaric Acid Cough Threshold in Non-Atopic Healthy Subjects. Thorax Aug. 1990;45(8):633-4.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Fukuyama T. Umezaki T, Shin T. Detection of Laryngeal Sensory-Evoked Potentials (LSEPs) in the Cat. Oct. 1993 Amer. Academy of Otolaryngology, pp. 748-752.

Fuller R. Hansson L. Karlsson JA. Neurophysiology of the Cough Reflex [Letter]European Respiratory Journal. 9(3):622-4, Mar. 1996.

Gerhardt T, Bancalari E. Maturational Changes of Reflex Influencing In Newborns. Amer. Physiological Society 1981. pp. 1282-1285.

Glogowska M. Stransky A., Widdicombe JF. Reflex Control of Discharge in Motor Fibers to the Larynx. Journal of Physiology. 239(2):368-79, Jun. 1974.

Guyton AC. Testbook of Medical Physiology (1991, 8th ed.) pp. 402-413.

Guz A, Noble MIM, Widdicombe JF. Trenchard D. Mushin WW. Peripheral Chemoreceptor Block in Man. Respiration Physiology. 1(1):38-40, 1966.

Guz A, Noble MIM, Widdicombe JF, Trenchard D., Mushin WW, Markey AR. The Role of Vagal and Glossopharyngeal Afferent Nerves in Respiratory Sensation, Control of Breathing and Arterial Pressure Regulation in Conscious Man. Clinical Science. 30(1): 161-70, Feb. 1966.

Hanacek J, Widdicombe JF. Influence of Lung Stretch Receptors on the Cough Reflex in Rabbits, 1983 Lung Stretch and Coughs, pp. 161-168.

Hardy SG. Medullary Projections to the Vagus Nerve and Posterolateral Hypothalamus. Anatomical Record Jun. 1995; 242(2):251-8.

Hedges JE, Bridges CJ. Stimulation of the Cough Reflex. American Journal of Nursing. 68(2);347-8, Feb. 1968.

Holstege G. Meiners L, Tan K. Projections of the Bed Nucleus of the Stria Terminalis to the Mesencephalon, Pons and Medulla Oblongata in the Cat. Experimental Brain Research 1984;58(2):379-91.

Hopkins DA, Holstege G. Amygdaloid Projections to the Mesencephalon, Pons and Medulla Oblongata in the Cat. Experimental Brain Research Aug. 15, 1978; 32(4):529-47.

Horner J. Brawer SR, Massey EW. Aspiration in Bilateral Stroke Patients: A Validation Study. Neurology. 43(2):43-3, Feb. 1993.

Horner J, Buoyer FG, Alberts MJ, Helm MJ. Dysphagia Following Brain-Stem Stroke: Clinical Correlates and Outcome. Archives of Neurology Nov. 1991; 48(11):1170-3.

Horner J, Massey EW. Silent Aspiration Following Stroke. Neurology. 38(2):317-9, Feb. 1988.

Horner J, Massey EW. Brazer SR. Aspiration in Bilateral Stroke Patients. Neurology, 40(11):1686-8, Nov. 1990.

Horner J. Massey EW, Riski JE, Lathrop DL, Chase KN. Aspiration Following Stroke: Clinical correlates and Outcome. Neurology. 38(9):1359-62, Sep. 1988.

Iscoe S, Feldman JL, Cohen MI. Properties of Inspiratory Termination by Superior Laryngeal and Vagal Stimulation. Respiration Physiology. 35(3):535-66, Apr. 1979.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Javorka K, Tomori Z, Zavarska L. 1985 Upper Airway Reflexes in Newborns with Respiratory Distress Syndrome. pp. 345-349.

Javorka K. Tomori Z. Zavarska L. 1980 Protective and Defensive Airway Reflexes in Premature Infants. Physiologia Bohemoslovaca pp. 29-35.

Jean A. Brainstem /Control of Swallowing: Localization and Organization of the Central Pattern Generator for Swallowing. 1990 Neurophysiology of the Jaws and Teeth. pp. 294-321.

Jean A, Car A. Roman C. Comparison of Activity in Pontine Versus Medullary Neurones During Swallowing. Experimental Brain Research. 22(2):211-20, 1975.

Jordan D, Donoghue S, Spyer KM. Respiratory Modulation of Afferent Terminal Excitability in the Nucleus Tractus Solitarius. Journal of the Autonomic Nervous System. 3(2-4:2991-7, Apr. 1991.

Jeffery PK. Korpas J. Widdicombe JF. Intraepithelial Nerve Fibers of the Cat Larynx and the Expiration Reflex [Proceedings]. Journal of Physiology. 275:35P-36P, Feb. 1978.

Kamei J. Hosokawa T. Yanaura S, Hukuhara T. Involvement of Central Sertonergic Mechanisms in the Cough Reflex. Japanese Journal of Pharmacology. 42(4):531-8, Dec. 1986.

Kamei J, Hukuhara T. Kasuya Y. Dopaminergic Control of the Cough Reflex as Demonstrated by the Effects of Apomorphine. European Journal of Pharmacology. 141(3):511-3, Sep. 23, 1987.

Karlsson JA. Airway Anaesthesia and the Cough Reflex. [Review] Bulletin European de Physiopatholgie Respiratoire. 23 Suppl 10:29s-36s. 1987.

Karlsson JA. Hanson L, Wollmer P, Dahlback M. Regional Sensitivy of the Respiratory Tract to Stimuli Causing Cough and Reflex Bronchoconstriction. Respiratory Medicine Jan. 1991;85 (Supplement A) 47-50.

Karlsson JA, Sant Ambrogio, Widdicombe J. Afferent Neural Pathways in Cough and Reflex Bronchoconstriction. Journal of Applied Physiology Sep. 1988;65(3):1007-23.

Katsumata U, Sekizawa K, Ebihara T, Sasaki H. Aging Effects on Cough Reflex [letter]. Chest 107(1)290-1, Jan. 1995.

Kearney HL. Unusual Cases of Cicatricial Stricture of the Esophagus. 1934 OTOL pp. 527-531.

Kessler JP, Jean A. Inhibition of the Swallowing Reflex by Local Application of Serotonergic Agents into the Nucleus of the Solitary Tract. European Journal of Pharmacology. 118(1-2:77-84), Nov. 26, 1985.

Kim YH. Hong WO, Kim KM, Kim HY. 1997 Superior Laryngeal Nerve Brain Stem Evoked Response in the Cat. Ann. Otol. Thinol. Laryngol. 106:101-8.

Korpas J. Recent Advances Concerning the Cough Reflex (Chairman's Introduction). [Review]Acta Physiologica Hungarica. 70(2-3;161-5, 1987.

Korpas J, Widdicombe JG. Aspects of the Cough Reflex [Review]Respiratory Medicine. 85 Suppl A:3-5, Jan. 1991.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Lalakea ML, Anonsen CK. Hannley M. Laryngeal Brainstem Evoked Response: A Developmental Study. Laryngoscope 100: Mar. 1990, pp. 294-301.

LeFrock JL, Clark TS, Davies B, Klainer AS. Aspiration Pneumonia. A Ten-Year Review, The American Surgeon May 1979.

Lemere F. Innervation of the Larynx I. Innervation of Laryngeal Muscles. The American Journal of Anatomy, vol. 51, No. 2, pp 417-437.

Lemere F. Innervation of the Lavrnx. II. Ramus Anastomoticus and Ganglion Cells of the Superior Laryngeal Nerve. American Journal of anatomy 1932; 54:389-407.

Lewis DJ, Prentice DE. The Ultrastructure of a Rat Laryngeal Epithelia. Journal of Anatomy 1980; 130:617-32.

Lowey AD, Burton H. Nuclei of the Solitary Tract: Efferent Projections to the Lower Brain Stem and Spinal Cord of the Cat. Journal of Comparative Neurology Sep. 15, 1978:181(2):421-49.

Lucier GE, Egizil R. Dostrovsky JO. 1986 Projections of the Internal Branch of the Superior Laryngeal Nerve of the Cat. Brain Res. Bull. 15:713-21.

Manchanda AK, Aneia IS. Afferent Projections of Superior Laryngeal Nerve in the Medulla Oblongata--Localization of the `Swallowing Centre`. Indian Journal of Physiology & Pharmacology. 16(1):67-73, Jan 1972.

Mantvh PW, Hunt SO. Neuropeptides are Present in Projection at all Levels in Visceral and Taste Pathways: from Periphery to Sensory Cortex. Brain Research. 99(2)297-312, May 14, 1984.

Mathew OP, SantAmbrogio G, Fisher JT, Sant Ambrogio FB. Respiratory Afferent Activity in the Superior Laryngeal Nerves. Respiration Physiology (1984 58, 41-50.

Matsumoto S. The Activities of Lung Stretch and Irritant Receptors During Cough. Neuroscience Letters, 90 (1988) 125-129.

McRitchie DA, Tork I. The Internal Organization of the Human Solitary Nucleus. Brain Research Bulletin 1993;31 (1-2):171-93.

Mei NN. Nourigat B. Etude Electrophysiologique des Neurones Sensitifs du Nerf Laryne Superieur. [Electrophysiologic Study of the Sensory Neurons of the Superior Laryngeal Nerve]. comptes Rendus des Seances de la Societe de Biologie et de Ses Filliales Jul. 1968; 162(1):149-53.

Miller AD, Bianchi AL, Bishol BO (eds). 1997 Neural Control of the Respiratory Muscles. Boca Raton CRC Press.

Miller AJ, Loizzi RF. Anatomical and Functional Differentiation of Superior Laryngeal Nerve Fibers Affecting Swallowing and Respiration. Experimetal Neurology Feb. 1974;42(2):369-87.

UNITED STATES PATENT AND TRADEMARK OFFICE
CERTIFICATE OF CORRECTION

PATENT NO.    : 6,561,195 B2
DATED         : May 13, 2003
INVENTOR(S)   : W. Robert Addington, Robert E. Stephens and Stuart P. Miller It is certified that error appears in the above-identified patent and that said Letters Patent is hereby corrected as shown below:

Montalt J, Basterra J, Armengot M, Barona R. Superior Laryngeal Nerve Evoked Potentials: An Experimental Study in the Rabbit. Laryngoscope 104:May 1994, pp. 627-630.

Morice AH, Higgins KS. Yeo WW. Adaptation of Cough Reflex with Different Types of Stimulation. European Respiratory Journal. 5(7)841-7, Jul. 1992.

Neafsey EJ. Hurley-Guis KM Aranitis D. The Toppgraphical Organization of Neurons in the Rat Medial Frontal, Insular and Olfactory Cortex Projecting to the Solitary Nucleus Olfactory Bulb, Periaqueducatal Gray and Superior Colliculas. Brain Research. 377(2):561-70, Jul. 9,1986.

Nishino T, Tagaito Y, Isono S. Cough and Other Reflexes on Irritation of Airway Mucosa in Man. Pulmonary Pharmacology (1996) 9, 285-292.

Nosaka S. Solitary Nucleus Neurons Transmitting Vagal Visceral Input to the Forebrain Via a Direct Pathway in Rats. Experimental Neurology Sep. 1984;84(3):493-505.

O'Connell F, Thomas VE, Pride NB. Adaptation of Cough Reflex with Different types of Stimulation [letter comment]. European Respiratory Journal. 5(10):1296-7, Nov. 1992.

"FDA Request for Designation", printed Apr. 8, 1998; Sponsor: Dysphagia Systems, Inc. pp. 1-19.

"Pneumoflex Neuroscientific Description", FDA Neuroscientific Master, printed Apr. 7, 1998; pp. 1-6.

Pneumoflex--Research Studies on the Safety and Nature of L-Tartaric Acid;--Safety and Scientific Studies; Dysphagia Systems, Inc. pp. 1-22.

Addington WR, Stephens RE, Gilliland K and Miller SP, "Tartaric Acid-Induced Cough and the Laryngeal Evoked Potential", pp. 1-14.

Addington, WR. Stephens, RE and Goulding RE. anesthesia of the Superior Laryngeal Nerve and Tartaric Acid-Induced Cough. pp. 1-15.

Stephens RE, Wendel KH and Addington, WR. "The Laryngeal Evoked Potential (LEP) and Laryngeal Cough Reflex", 28 pages.

Addington WR, Stephens RE, Gillilnd K and Rodriguez M. "Assessing the Laryngeal Cough Reflex an the Risk of Devleoping Pneumonia After Stroke." pp. 1-22.

Pack R.J., Al-Ugaily L.H. Widdicombe J.G. -The innervation of the trachea and extrapulmonary bronchi of the mouse. Cell & Tissue Research. 238(1): 61-8, 1984.

Paintal A.S.,-Vagal Sensory Receptors and their Reflex Effects. Physiological Review 1973; 53(1): 159-225 Jan.

Palmer J.B., Duchane A.S.-1991. Rehabilitation of Swallowing Disorders Due to Stroke. Physical Medicine and Rehabilitation Clinics of North America 1991 2(3) 529-546.

Pantaleo T. Corda M.-Expiration-related Neurons in the Region of the Retrofacial Nucleus: Vagal and Laryngeal Inhibitory Influences. Brain Research Dec. 16, 1985; 359(1-2): 343-6.

Pimpaneau A. O'Brien J., Albe-Fessard D.-Afferences du Nerf Larynge Superieur et du Nerf Vague Vers les Aires Corticales de Projections et de Commande de la face, de la Langue et Larynx Chez le Singe. Journal de Physiologe 1967; 59 (4 Suppl): 474

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Sant' Ambrogio g.-Afferent Pathways for Cough Reflex. [Review] Bulletin European de Physiopathologie Respiratorie 1987; 23 (Suppl 10): 19s-23s.

Sant' Ambrogio g.-1996. Role of the Larynx in Cough.

Sant' Ambrogio G., Mathew O.P., Sant' Ambrogio F.B.-Role of Intrinsic Muscles and Tracheal Motion In Modulating Laryngeal Receptors. Respiration Physiology. 6l(3): 289-300, Sep. 1985.

Sant' Ambrogio G., Sant' Ambrogio F. B., Davies A.-Airway Receptors in Cough. Bulletin European de Physiopathologie Respiratoire Jan.-Feb. 1984; 20(1): 43-7.

Sant' Ambrogio G., Sant' Ambrogie F. B.,-(1996) Role of Laryngeal Afferents in Cough.

Sant' Ambrogio G.G., Tsubone H., Sant' ambrogio F.B.-Sensory Information from the Upper Airway: Role in the Control of Breathing. [Review] Respiration Physiology Oct. 1995; 102(1): 1-16.

Sasaki, C.T. Newman A., Akitaya T., Kirchner J.A.-Effect of Microaerosol Inhalation on the Pattern of Breathing. Annals of Otology, Rhinology & Laryngology. May-Jun. 1975 84(3 pt 1): 344-9.

Sato L. Shimada K. 1995 Arborization of the Inferior Laryngeal Nerve and Internal Nerve on the Posterior Surface of the Larynx. Clin. Anat. 8:379-387.

Schugt H. P. The Piriform Sinus: Anatomic and Clinical Observations with a Review of the Literature. Arch. Otol. 1940; 31: 626-14.

Sekizawa K., Ujiie Y., Nakazawa H., Sasaki H., Sasaki H. Katsumata U., Takasugi R. Abnormalities in Cough Reflex.

Sellick H., Widdicombe, J.G. Vagal Deflation and Inflation Reflexes Mediated by Lung Irritant Receptors.

Sessle, G. J. Ball, G. J., Lucier, G. E., Suppressive Influences from Periaqueductal Gray and Nucleus Raphe Magnus on Respiration and Related Reflex Activities and on Solitary Tract Neurons, and Effect of Naloxone. Brain Research--216 (1981) 145-161.

Shannon. R., Bolser, D. C., Lindsey, G. G. 1997 Neural Control of Coughing and Sneezing. In Neural Control of the Respiratory Muscles. A. D. Miller, A. L. Bianchi, and B. P. Bishop (eds.) Boca Raton: CRC Pres, pp. 216-19.

Simonsson. G. B., Jacobs, F. M., Nadel, J.A. Role of Autonomic Nervous System and the Cough Reflex in the Increased Responsiveness of Airways in Patients with Obstructive Airway Disease. Journal of Clinical Investigation. 46(11): 1812-8, Nov. 1967.

Stockwell, M., Lang, Yip, R., Zintel, T., White C., Gallagher, C. G. Lack of Importance of the Superior Laryngeal Nerves in Citric Acid Cough in Humans. Journal of Applied Physiology. 75(2): 613-7, Aug. 1993.

Stockwell, M., Lazanoff, S., Lang, S., Nyssen, J. Superior Laryngeal Nerve Block: An Anatomical Study. 1995 Clinical Anatomy 8:89-95.

Stransky, A., Szereda-Przestaszewska, M., Widdicombe, J.G. The Effects of Lung Reflexes on Laryngeal Resistance and Motoneurone Discharge. J. Physiol (1973) pp. 417-438.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Suziki M., Sasaki, C. T. Effect of Various Sensory Stimuli on Reflex Laryngeal Adduction. Annals of Otology, Rhinology & Laryngology Jan.-Feb. 1997; 86(1 pt 1): 30-6.

Suzuki, M., Sasaki, C. T. Initiation on Reflex Glottic Closure. Annals of Otology, Rhinology & Laryngology May-Jun. 1976; 85 (3 pt 1): 382-6.

Suzuki, M., Kirchner, J. A. Sensory Fibers in the Recurrent Laryngeal Nerve: An Electrophysiological Study of some Laryngeal Afferent Fibers in the Recurrent Laryngeal Nerve of the Cat. II, pp. 21-30.

Szereda-Przestaszewska, M., Widdicombe, J.G. Reflex Changes in the Lumen of the Cat Larynx Due to Chemical Irritation of the Upper Airways. Journal of Physiology-- July 1973; 232(2): 80p-81p.

Takagi S., Umezaki, T., Shin, T. Convergence of Laryngeal Afferents with Different Natures Upon Cat NTS Neurons. Brain Research Bulletin--vol. 38. No. 3, pp. 261-268, 1995.

Takshama K., Miyata, T. [Cough--Diversity and the Peripheral Mechanisms of Production]. Nippon Yakurigaku Zasshi--Folia Pharmacologica Japonica Feb. 1995; 105(2): 41-52.

Tatar, M., Sant' Ambrogio, G., Sant' Ambrogio, F. B. Laryngeal and Tracheobronichial Cough in Anesthetized Dogs.

Tell, F., Fagni L, Jean, A. Neurons of the Nucleus Tractus Solitarius, in Vitro, Generate Bursting Activities by Solitary Tract Stimulation. Exp. Brain Res. (1990) 79: 436-440.

Terreberry, R. R. Neafsey, E/J. Rat Medial Frontal Cortex: A Visceral Motor Region with a Direct Projection to the Solitary Nucleus. Brain Research Nov. 14, 1983; 278 (1-2): 245-9.

Tereberry, R.R. Neafsey, E.J. The Rat Medial Frontal Cortex Projects Directly to Autonomic Regions of the Brainstem. Brain Research Bulletin Dec. 1987; 19 (6); 639-49.

Traxel. R.M., Prudlow, W. F., Kampine J.P., Coon, R.L., Zuperku, E.J. Annals of Otology, Rhinology 7 Laryngology. 85(5 pt. 1): 664-9, 1976 Sep.-Oct.

Twitchell, T.E. The Restoration of Motor Function Following Hemiplegia in Man. Brain 1951; 443-80.

van de Kooy, D., Koda, L.Y., McGinty, J.E., Gerfen, C. R, Bloom F.E. The Organization of Projections from the Cortex, Amygdala, and Hypothalamus to the Nucleus of the solitary Tract in Rat. Journal of Comparative Neurology Mar. 20, 1984: 224(1): 1-24.

van der Kooy, D., McGinty, J.F., Koda, L.Y., Gerfen, Bloom, F.E. Visceral Cortex: A Direct Connection from Prefrontal Cortex to the Solitary Nucleus in Rat. Neuroscience Letters 1982: 33(2): 123-7.

Vogel, P.H.--The Innervation of the Larynx of Man and the Dog. II. Ramus Anastomoticus and Ganglion Cells of the Superior Laryngeal Nerve. American Journal of Anatomy 1952; 90: 427-47.

Weerasuriva, A., Bieger, D., Hockman, C.H.--Basel Forebrain Facilitation of Reflex Swallowing in Cat. 1979 Brain Res 174: 119-133.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Widdicombe, J.G.--Sensory Neurophysiology of the Cough Reflex. 1996 J Allergy Clin Immunol 98 (5 part 2): s84-s90.

Widdicombe, J.G.--Neurophysiology of the Cough Reflex 1995 Eur Respir J 8:1193-1202.

Widdicombe, J.G.--Mechanism of Cough and its Regulation [Review] European Journal of Respiratory Diseases--Supplement 110:11-20, 1980.

Widdicombe, J.G.--Nasal and Pharygneal Reflexes: Protective and Respiratory Functions. In Respiratory Function of the Upper Airway. G. Sant' Ambrogio and O.P. Mathew, Eds. Marcel Drekker, N.Y. 1988; pp. 233-58.

Widdicombe, J.G.--Reflexes from the Lungs and the Respiratory Tract. 1971 Acta Physiologica Polonica 22 (3 suppl 2): 397-418.

Widdicombe, J.G.--Sensory Innervation of the Lungs and Airways. Progress in Brain Research 1986; 67;49-64.

Widdicombe, J.G., --Studies on Afferent Airway Innervation. American Review of Respiratory Disease 1977: 115(6 pt 2): 99-105.

Widdicombe, J.G.--Modes of Excitation of Respiratory Tract Receptors. Progress in Brain Research 1976; 43:243-52.

Widdicombe, J.G.--Pulmonary and Respiratory Tract Receptors 1982 J Exp. Biol 100:41-57.

Widdicombe, J.G.--Mediators of Reflexes and Bronchoconstriction [Review] European Journal of Respiratory Diseases--Supplement 129:65-94, 1983.

Widdicomber, J.G.--Chemoreceptor Control of Airways 1992--Respiration Physiology 87:373-81.

Widdicomber, J.G.--Lungs and Inspiratory Tract Afferences. Introductory Talk. pp. 233-40. In: Duron B., ed Respiratory Centers and Afferent Systems. Paris, INSERM, 1976.

Widdicombe, J.G. [Laryngeal Receptors in the Expiratory Reflex] 1986 Bratislavske Lekarske Listy 85(4): 424-9.

Widdicombe, J.G.--Proceedings: Reflex Control of Larnynx. Bulletin de Physio-Patholgie Respiratorie 11(2): 102P-103P, Mar.-Apr 1975 .

Widdicombe, J.G.--Pathophysiology of Lung Reflexes. Bulletin de Physio-Pathologie Respiratorie. 10(1):65-9, Jan-Feb. 1974.

Widdicombe, J.G.--Lung Reflexes. Bulletin de Physio-Pathologie Respiratorie 8(3): 723-5, May-Jun. 1972.

Widdicombe, J.G.--Reflex Function of the Lung: Round Table Discussion. Bulletin de Physio-Pathologie Respiratorie. 10(1): 85-7, Jan-Feb. 1974.

Widdicombe, J.G. Glogowska, M, --Relative Roles of Irritant, Type--J and Pulmonary Stretch Receptors in Lung Reflexes 1973 Acta Neurobiol Exp 33:21-31.

Widdicombe, J.G., Sant' Ambrogio, G., Mathew, O.P.--Nerve Receptors of the Upper Airway, In Respiratory Function of the Upper Airway. G. Sant' and O.P. Mathew, Eds, Marcel Drekker, NY 1988; pp. 193-231.

Widdicombe, J.G., Sterling, G.M.,--The Autonomic Nervous System and Breathing [Review] 1970 Archives of Internal Medicine 126:311-29.

UNITED STATES PATENT AND TRADEMARK OFFICE
CERTIFICATE OF CORRECTION

PATENT NO. : 6,561,195 B2
DATED : May 13, 2003
INVENTOR(S) : W. Robert Addington, Robert E. Stephens and Stuart P. Miller It is certified that error appears in the above-identified patent and that said Letters Patent is hereby corrected as shown below:

Widdicombe, J.G., Tartar, M.--Upper Airway Reflex Control. Annals of the New York Academy of Sciences 1988; 533:252-61.

Yamamoto, Y., Hosono, L. Atoji. Y., Susuki, Y.--Morphological Study of the Vagal Afferent Nerve Endings in the Laryngeal Mucusa of the Dog 1997 Anatomischer Anzeiger 179: 65-73.

Yanaura, S., Hosokawa, T., Kitagawa , H. Yamatake, Y.,--Influence of Tracheal Muscular Tone on the Initiation of Cough Reflex 1978 Japan J. Pharmacol 28(3): 447-455.

Yanaura, S., Kamei, J., Goto, K, Hosokawa, T., Hiramori T., Misawa, M., Hukuhara, T.,--A Quantitative Analysis of the Phrenic Nerve Activities During the Cough Reflex 1982 Folia Pharmacol Japan 79: 543-550.

Yanaura, S., Iwase, H., Sato, S., Nishimura, T.--A New Method for Induction of the Cough Reflex 1974 Japan J. Pharmacol 24(3) 453-460.

Yanaura S., Nishimura, T., Sasao, T., Sone, Y.--Proceedings: Pharmacolgical Studies of the Respiratory Tract. 9. A Study of Cough-Like Reflex. 1974 Japanese Journal of Pharmacology. 24:s29.

Yanaura, S., Nishimura, T. Hosokawa, T., Abe Y., Iwase, H.--Pharmacological Studies on the Cough-Like Reflex Induced by Chemical Stimulation. [Japanese] Nippon Yakurigaku Zasshi--Folia Pharmacologica Japonica. 74(3): 345-52, Apr. 1978.

Yanaura, S. Hosokawa, T., Kitagawa, H., Kamei. J., Misawa, M.--Effects of Peripheral Airway Response on the Cough Reflex. [Japanese] Nippon Yakurigaku Zasshi--Folia Pharmacolgica Japonica 76(8): 709-16, Nov. 1980.

Yunaura, S., Hosokawa, T., Kitagawa, H., Misawa, M.--Reflex on the Tracheobronichial Vascular Tone. [Japanese] Nippon Yakurigaku Zasshi--Folia Pharmacologica Japonica. 78(1): 9-16, Jul. 1981.

Yin, S.S., Qiu, W.W., Strucker, F.J., Hoasjoe, D.K., Aarstad, R.F., Batchelor, B.M., --1997 Laryngeal Evoked Brainstem Responses in Humans: A Prelininary Study. Laryngoscope 107:1261-6, Sep. 1997.

Yoshida Y., Tanaka Y., IMitsumasu, T., Hirano, M. Kanaseki, T.--1986 Peripheral Course and Intramucosal Distribution of the Laryngeal Sensory Nerve Fibers of Cats. Brain Research Bulletin 17:95-105.

Zelenak, J.P., Alarie lY., Weyel, D.A.--Assessment of the Cough Reflex Caused by Inhalation of Sodium Lauryl Sulfate and Citric Acid Aerosols. Fundamental & Applied Toxicology. 2(4): 177-80. Jul.-Aug. 1982.

Rogers, R.C., Nelson, D.O.--Neurons of the Vagal Division of the Solitary Nucleus Activated by the Paraventricular Nucleus of the Hypothalamus. Journal of the Autonomic Nervous System Apr. 1984; 10(2): 193-7.

Sekizawa, K. Yjiie, Y., Itabashi, S., Sasaki, H., Takishima, T.--Lack of Cough Reflex in Aspiration Pneumonia [Letter] Lancet May 19, 1990;335 (8699):1228-9.--

UNITED STATES PATENT AND TRADEMARK OFFICE
CERTIFICATE OF CORRECTION

PATENT NO.    : 6,561,195 B2
DATED         : May 13, 2003
INVENTOR(S)   : W. Robert Addington, Robert E. Stephens and Stuart P. Miller It is certified that error appears in the above-identified patent and that said Letters Patent is hereby corrected as shown below:

Column 6,
Line 19, delete "583" insert -- 563 --
Line 30, delete "533" insert -- 563 --

Column 7,
Line 21, delete "grouping" insert -- group --

Signed and Sealed this

Sixth Day of January, 2004

JAMES E. ROGAN
*Director of the United States Patent and Trademark Office*